United States Patent [19]

Bledsoe, Jr. et al.

[11] Patent Number: 4,853,089

[45] Date of Patent: Aug. 1, 1989

[54] PROCESS FOR PURIFYING EXO-2-HYDROXY-1,4 CINEOLE

[75] Inventors: James O. Bledsoe, Jr.; Bernard Brust, both of Jacksonville, Fla.

[73] Assignee: Union Camp Corporation, Wayne, N.J.

[21] Appl. No.: 114,883

[22] Filed: Oct. 29, 1987

Related U.S. Application Data

[63] Continuation-in-part of Ser. No. 874,536, Jun. 16, 1986, abandoned.

[51] Int. Cl.$^4$ .............................................. B01D 3/34
[52] U.S. Cl. ........................................ 203/38; 203/59; 203/71; 203/DIG. 6; 568/664
[58] Field of Search ............ 203/38, 59, 71, 33, 203/14, 32, DIG. 6; 568/664; 549/463

[56] References Cited

U.S. PATENT DOCUMENTS

| | | | |
|---|---|---|---|
| 2,204,956 | 6/1940 | Bresler et al. | 203/38 |
| 2,377,714 | 6/1945 | Perkins | 568/664 |
| 2,700,059 | 1/1955 | Hall et al. | 568/664 |
| 2,826,537 | 3/1958 | Sharp et al. | 203/38 |
| 2,900,311 | 8/1959 | Montagna | 203/38 |
| 3,819,492 | 6/1974 | Stevenson et al. | 203/38 |
| 3,849,262 | 11/1974 | Cocuzza | 203/38 |
| 3,917,652 | 11/1975 | Pawson et al. | 549/453 |
| 4,487,945 | 12/1984 | Payne | 549/463 |
| 4,525,203 | 6/1985 | Payne et al. | 549/273 |
| 4,602,933 | 7/1986 | Pilgram | 549/332 |
| 4,602,934 | 7/1986 | Pilgram | 549/331 |

*Primary Examiner*—Kenneth M. Schor
*Assistant Examiner*—V. Manoharan
*Attorney, Agent, or Firm*—Edward J. Sites

[57] ABSTRACT

A process for purifying exo-2-hydroxy-1,4-cineole contaminated with ketones is carried out by derivatizing the ketone to form a compound readily separable from the desired cineole, either by distillation, solvent extraction or like separation process. In one embodiment method of the invention, derivatization is carried out by reaction of the ketone with an amine. The amine reacts with the ketone impurities to form water and relatively stable enamine derivatives that have a much lower vapor pressure than the exo-2-hydroxy-1,4-cineole. The desired product may then be separated by distillation.

17 Claims, No Drawings

PROCESS FOR PURIFYING EXO-2-HYDROXY-1,4 CINEOLE

CROSS-REFERENCE TO RELATED APPLICATION

This application is a continuation-in-part of copending U.S. Pat. application Ser. No. 874,536 filed June 16, 1986, now abandoned.

BACKGROUND OF THE INVENTION

1. Field of the Invention

The invention relates to an improved method of purifying exo-2-hydroxy-1,4-cineole.

2. Brief Description of the Prior Art

Exo-2-hydroxy-1,4-cineole is a well known compound useful for example as an intermediate in the preparation of herbicides. The commercially produced exo-2-hydroxy-1,4-cineole generally contains appreciable presence of contaminant ketones which are undesirable for many uses of the cineole. It is therefore important in such applications that the purity of the cineole be high. However the ketone impurities are generally ones that have vapor pressures close to that of the cineole and cannot normally be separated by fractional distillation. More costly recrystallization techniques are often necessary.

The present invention enables one to purify exo-2-hydroxy-1,4-cineole, obtaining the desired product with up to 99+% purity, with economic advantages.

SUMMARY OF THE INVENTION

The invention comprises a method of purifying exo-2-hydroxy-1,4-cineole contaminated with a ketone, which comprises; reacting the ketone with a reagent to form a derivative of the ketone which is readily separable from the exo-2-hydroxy-1,4-cineole; and separating the exo-2-hydroxy-1,4-cineole from the reaction product.

The method of the invention provides a high purity product without the need for recrystallization and the attendant equipment and solvents.

DETAILED DESCRIPTION OF THE INVENTION

The method of the invention may be carried out by reacting an amine with the ketone impurity and separating the desired product from the reaction mixture. The reaction may be carried out at ambient temperature, but is preferably carried out at or below reflux temperatures for the reaction mixture. Any organic amine which will react wtih a ketone to form an enamine and having a boiling point substantially apart from the boiling point for the exo-2-hydroxy-1,4-cineole may be advantageously used. Representative of organic amines advantageously employed are:

EDA—ethylenediamine ($H_2NC_2H_4NH_2$)
DETA—diethylenetriamine ($H_2N(C_2H_4NH)_2H$)
TETA—triethylenetetramine ($H_2N(C_2H_4NH)_3H$)
EDX—polyaminopropylethylenediamine
($H_2NCH_2CH_2CH_2NHCH_2CH_2[NHCH_2CH_2] \times NH_2$)
MEA—monoethanolamine ($HOCH_2CH_2NH_2$) and the like. TETA is a preferred amine since its boiling point (277° C.) is high enough for the exo-2-hydroxy-1,4-cineole to be distilled from it, but not so high that its eventual recovery for reuse would be difficult.

The function of the amine is to scavenge the ketone impurities (i.e. ketone, diketone, and hydroxyketone) by reacting with them and thus forming water and relatively stable enamine derivatives. These enamines have a much lower vapor pressure than the exo-2-hydroxy-1,4-cineole and facilitate separation by distillation.

It is advantageous that the water of reaction be removed during the formation of the enamines. The water removal shifts the reaction equilibrium so that substantially all the ketone impurities are derivatized as enamines. The water may be removed by azeotropic distillation.

Toluene may be employed as an azeotrope.

Once the water of reaction is removed, exo-2-hydroxy-1,4-cineole may be distilled away from excess amine, and enamine. The first distilled exo-2-hydroxy-1,4-cineole may then be fractionated on a distillation column to obtain exo-2-hydroxy-1,4-cineole with a purity as high as 99+%. The bottoms product may be processed separately to regenerate the amine and ketone impurities and recover the amine for recycle since the reaction between the amine and the ketone is reversible by the addition of water to the bottoms mixture. The amine is recoverable by distillation.

The proportion of organic amine added to the ketone containing mixture with the exo-2-hydroxy-1,4-cineole is one sufficient to react with all of the ketone impurities, preferably an excess molar proportion.

In another embodiment method of the invention, the mixture of exo-2-hydroxy-1,4-cineole and the ketone impurity is admixed with a mixture of sodium bisulfite and sodium bicarbonate to form the bisulfite derivative of the ketone impurity. The derivative will form at room temperatures but the rate of reaction will be increased by heating the reaction mixture, advantageously up to a temperature of about 200° C. The proportion of sodium bisulfite and sodium bicarbonate added to the mixture for separation is that proportion which is sufficient to react with ketone present with the bisulfite, forming an adduct. The exact proportion will of course depend on the amount of ketone present, which may be determined by conventional analysis. The derivative adduct is water soluble and upon completion of the derivatization, the bisulfite derivative of the ketone may be separated by extraction into water, leaving the desired exo-2-hydroxy-1,4-cineole, free of impurity.

A variation of the method employing a bisulfite derivatization comprises carrying out the derivatization in the presence of a weak acid such as formic or cetic acid to promote formation of the water-soluble adduct.

Another embodiment method of the invention, employing water solubility to effect the separation of a ketone derivative, comprises admixture of the mixture containing the exo-2-hydroxy-1,4-cineole and the ketone with (carboxymethyl) trimethylammonium chloride hydrazide (Girard's Reagent-T). The Girard Reagent-T reacts with ketone at ambient to slightly elevated temperatures to form a hydrazone. The hydrazone has water solubility allowing it to be separated by water extraction from the exo-2-hydroxy-1,4-cineole.

The following examples describe the manner and the process for making and using the invention and set forth the best mode contemplated by the inventors for carrying out the invention, but are not to be construed as limiting.

EXAMPLE 1

To a crude mixture of toluene and 2-hydroxy-1,4-cineole (10,175.2 g.) containing 33.6 wt. % exo-2-hydroxy-1,4-cineole and 5.8 wt. % 4-hydroxycarvomenthone is added 1590 g. of triethylenetetramine (TETA). The resulting mixture is heated to reflux (118° C.) under atmospheric pressure and water of condensation is removed in a Dean-Stark trap as it forms. A total of 179.2 g. of water is removed. Using a distillation head (no column) the toluene is stripped off under atmospheric pressure at a temperature of 150° C. A total of 4308.8 g. of toluene is recovered. Further toluene is removed under a pressure of 300 mm Hg up to a temperature of 150° C. Obtained is an additional 629.4 g. of toluene and 379.5 g. more toluene is collected in a dry-ice trap. Crude exo-2-hydroxy-1,4-cineole (6065.2 g.) containing 53.9 wt. % of exo-2-hydroxy1,4-cineole is obtained. This material is stripped under a pressure of 2 mm Hg and to obtain 3519.3 g. of product containing 81.6 wt. % exo-2-hydroxy-1,4-cineole free of ketone contaminants.

The following examples used the first-distilled 2-hydroxy-1,4-cineole obtained in Example 1. The recycle 2-hydroxy-1,4-cineole obtained in Example 2 below is added to the first-distilled feed and this combined material is distilled in Example 3. Likewise, the recycle 2-hydroxy-1,4-cineole obtained in Example 3 is added to the first-distilled feed and this combined material is distilled in Example 4.

|  | EXAMPLE 2 | EXAMPLE 3 | EXAMPLE 4 |
|---|---|---|---|
| IN |  |  |  |
| Wt. 1st distilled feed, g. | 1000 | 1000 | 1000 |
| Wt. % CNOH in Feed | 81.6 | 81.6 | 81.6 |
| Recycle, g. | — | 288.1 | 417.2 |
| Recycle, wt. % CNOH | — | 91.0 | 88.8 |
| OUT |  |  |  |
| 99+ wt. % CNOH, g. | 470 | 680.6 | 872.2 |
| Recycle (front & back), g. | 373.8 | 459.1 | 367.0 |
| Recycle, wt. % CNOH | 91.0 | 89.0 | 76.3 |
| Column Hold Up, Wt., g. | 158.1 | 152.5 | 193.0 |
| Wt. % CNOH | 21.0 | 22.9 | 23.0 |
| CNOH Accountability |  |  |  |
| Wt. % of 99+ wt. % CNOH obtained based on contained CNOH in feed and recycles | 57.6 | 63.1 | 73.5 |
| Overall wt. % CNOH accountability Not incl. column hold-up | 99.3 | 97.8 | 97.1 |

CNOH = exo-2-hydroxy-1,4-cineole

EXAMPLE 2

| | | Column used 4 ft. × 2 in. | | | Analysis | | |
|---|---|---|---|---|---|---|---|
| Fraction No. | Wt., g. | Kettle Temp., °C. | Head Temp., °C. | Reflux Ratio | Pressure mm Hg | % LE | % CNOH | % HB |
| 1 | 50.5 | 120 | 95 | 20:1 | 1.7 | 24.1 | 74.1 | 1.8 |
| 2 | 52.6 | 120 | 87 | 20:1 | 1.7 | 8.4 | 90.2 | 1.4 |
| 3 | 52.2 | 120 | 86 | 20:1 | 1.7 | 4.2 | 94.5 | 1.3 |
| 4 | 46.1 | 120 | 87 | 20:1 | 1.7 | 2.3 | 96.6 | 1.1 |
| 5 | 54.4 | 121 | 85 | 20:1 | 1.7 | 1.2 | 97.7 | 1.1 |
| 6 | 52.5 | 124 | 101 | 20:1 | 1.0 | 0.7 | 98.4 | 0.9 |
| 7 | 48.2 | 125 | 104 | 20:1 | 1.0 | 0.4 | 98.9 | 0.7 |
| 8 | 57.0 | 121 | 100 | 20:1 | 1.0 | 0.1 | 99.2 | 0.7 |
| 9 | 53.7 | 124 | 104 | 20:1 | 1.4 | 1.0 | 98.2 | 0.8 |
| 10 | 53.6 | 125 | 83 | 20:1 | 1.0 | 0.2 | 98.9 | 0.9 |
| 11 | 52.9 | 129 | 83 | 20:1 | 1.0 | — | 99.2 | 0.8 |
| 12 | 52.2 | 134 | 84 | 20:1 | 1.0 | — | 99.8 | 0.7 |
| 13 | 52.0 | 141 | 84 | 20:1 | 1.0 | 0.2 | 99.3 | 0.5 |
| 14 | 52.9 | 149 | 84 | 20:1 | 1.0 | 1.0 | 98.6 | 0.3 |
| 15 | 52.2 | 154 | 84 | 20:1 | 1.0 | 4.9 | 94.9 | 0.2 |
| 16 | 50.6 | 161 | 95 | 20:1 | 1.0 | 4.8 | 94.1 | 1.1 |
| 17 | 15.2 | 171 | 81 | 20:1 | 1.0 | 1.2 | 76.0 | 22.8 |
| Hold-up Fr. | 158.1 | — | — | — | — | — | 21.3 | 78.7 |
| 6-14 Fr. | 470.0 | — | — | — | — | .02 | 99.9 | 0.8 |
| 1-5 Fr. | 255.8 | — | — | — | — | — | — | — |
| 15-17 | 118.0 | — | — | — | — | — | — | — |
| Recycle 1-5, 15-17 | 373.8 | — | — | — | — | 6.8 | 91.0 | 2.2 |

LE = Light Ends
HB = High boilers

EXAMPLE 3

| Fraction No. | Wt., g. | Kettle Temp., °C. | Head Temp., °C. | Reflux Ratio | Pressure mm Hg | % LE | % CNOH | % HB |
|---|---|---|---|---|---|---|---|---|
| 1 | 50.0 | 110 | 75 | 10:1 | 1.5 | 29.7 | 68.6 | 1.7 |
| 2 | 50.4 | 116 | 80 | 10:1 | 1.5 | 21.8 | 76.4 | 1.9 |
| 3 | 52.5 | 117 | 80 | 10:1 | 1.5 | 11.9 | 86.4 | 1.6 |
| 4 | 48.9 | 120 | 85 | 10:1 | 1.4 | 7.2 | 91.6 | 1.2 |
| 5 | 51.2 | 118 | 85 | 10:1 | 3.4 | 4.7 | 94.1 | 1.2 |
| 6 | 46.4 | 118 | 87 | 10:1 | 2.4 | 2.7 | 96.2 | 1.1 |
| 7 | 51.6 | 118 | 87 | 10:1 | 3.5 | 1.9 | 97.1 | 1.0 |
| 8 | 51.2 | 119 | 89 | 10:1 | 3.4 | 0.9 | 98.1 | 1.0 |
| 9 | 53.5 | 119 | 86 | 10:1 | 3.5 | 0.6 | 98.4 | 1.0 |
| 10 | 50.3 | 118 | 85 | 10:1 | 3.5 | 0.4 | 98.7 | 0.9 |
| 11 | 52.6 | 119 | 88 | 10:1 | 3.5 | 0.2 | 98.9 | 0.8 |
| 12 | 53.2 | 120 | 88 | 10:1 | 3.2 | 0.1 | 99.1 | 0.8 |
| 13 | 51.9 | 120 | 90 | 10:1 | 3.2 | 0.1 | 99.2 | 0.7 |
| 14 | 51.7 | 120 | 91 | 10:1 | 3.2 | — | 99.3 | 0.7 |
| 15 | 52.5 | 125 | 90 | 10:1 | 3.0 | — | 99.4 | 0.6 |
| 16 | 51.6 | 126 | 89 | 10:1 | 3.4 | — | 99.4 | 0.6 |
| 17 | 51.6 | 130 | 89 | 10:1 | 3.4 | 0.2 | 99.3 | 0.5 |
| 18 | 51.1 | 140 | 90 | 10:1 | 3.4 | 0.4 | 99.3 | 0.3 |
| 19 | 55.5 | 145 | 93 | 10:1 | 2.8 | 1.0 | 99.0 | — |
| 20 | 53.9 | 158 | 95 | 10:1 | 3.4 | 1.4 | 98.6 | — |
| 21 | 56.4 | 163 | 100 | 10:1 | 3.4 | 4.4 | 95.6 | — |
| 22 | 51.7 | 200 | 109 | 10:1 | 3.4 | 3.2 | 92.4 | 4.4 |
| Fr. 8-20 | 680.6 | — | — | — | — | 0.2 | 99.2 | 0.6 |
| Fr. (1-7 + 21-22) | 459.1 | — | — | — | — | 8.0 | 89.0 | 2.0 |

EXAMPLE 4

| Fraction No. | Wt., g. | Kettle Temp., °C. | Head Temp., °C. | Reflux Ratio | mm Hg Pressure | % LE | % CNOH | % HB |
|---|---|---|---|---|---|---|---|---|
| 1 | 48.4 | 118 | 91 | 10:1 | 4.9 | 62.6 | 34.8 | 2.6 |
| 2 | 50.0 | 118 | 92 | 10:1 | 4.9 | 20.9 | 77.4 | 1.7 |
| 3 | 51.4 | 117 | 92 | 10:1 | 4.7 | 11.1 | 87.3 | 1.5 |
| 4 | 57.2 | 118 | 92 | 10:1 | 4.7 | 7.2 | 91.4 | 1.4 |
| 5 | 52.7 | 118 | 90 | 10:1 | 4.6 | 3.5 | 95.4 | 1.1 |
| 6 | 51.1 | 118 | 94 | 10:1 | 4.2 | 2.5 | 96.3 | 1.2 |
| 7 | 51.8 | 119 | 96 | 10:1 | 4.2 | 1.1 | 98.0 | 0.9 |
| 8 | 58.7 | 119 | 97 | 10:1 | 5.2 | 0.5 | 98.7 | 0.8 |
| 9 | 52.1 | 119 | 97 | 10:1 | 5.0 | 0.2 | 98.9 | 0.8 |
| 10 | 52.4 | 120 | 96 | 10:1 | 5.0 | 0.2 | 99.0 | 0.8 |
| 11 | 51.7 | 118 | 94 | 10:1 | 4.9 | 0.1 | 99.1 | 0.8 |
| 12 | 54.3 | 121 | 96 | 10:1 | 5.0 | 0.1 | 99.1 | 0.8 |
| 13 | 51.7 | 121 | 96 | 10:1 | 5.0 | — | 99.2 | 0.8 |
| 14 | 54.8 | 121 | 96 | 10:1 | 4.8 | — | 99.3 | 0.7 |
| 15 | 53.5 | 122 | 97 | 10:1 | 4.5 | — | 99.3 | 0.7 |
| 16 | 53.9 | 124 | 97 | 10:1 | 4.5 | — | 99.3 | 0.7 |
| 17 | 51.1 | 126 | 99 | 10:1 | 4.3 | — | 99.5 | 0.5 |
| 18 | 63.1 | 128 | 96 | 10:1 | 4.5 | 0.4 | 99.1 | 0.5 |
| 19 | 54.9 | 132 | 93 | 10:1 | 4.5 | 2.0 | 97.7 | 0.3 |
| 20 | 54.8 | 139 | 96 | 10:1 | 3.9 | 2.3 | 97.7 | — |
| 21 | 59.1 | 146 | 93 | 10:1 | 2.5 | 2.5 | 97.5 | — |
| 22 | 54.3 | 160 | 100 | 10:1 | 2.6 | 4.1 | 95.9 | — |
| 23 | 56.2 | 160 | 100 | 10:1 | 2.5 | 3.3 | 84.7 | 12.0 |
| Fr. 7-12 | 759.3 | — | — | — | — | 0.1 | 99.4 | 0.6 |

EXAMPLE 5

To a crude mixture of toluene and 2-hydroxy-1,4-cineole (11,498 g.) containing 27.3 wt. % exo-2-hydroxy-1,4-cieole and 3.3 wt. % 4-hydroxycarvomenthone is added 1025 g. of triethylenetetramine (TETA). The resulting mixture is heated to reflux (118° C.) under atmospheric pressure and water and toluene is removed by stripping through a distillation head at a temperature of 160° C. A Dean-Stark trap is added to remove any additional water formed. A total of 24.1 g. of water is removed in this step. Additional toluene (499.1 g.) is then stripped under a pressure of 250 mm Hg. The crude residue remaining is 5,586.6 g. containing 60.0 wt. % exo-2-hydroxy-1,4-cineole. This residue is stripped under a pressure of 2 mm Hg to obtain 2982.1 g. of product containing 85.2 wt. % exo-2-hydroxy-1,4-cineole free of ketone contaminants.

EXAMPLE 6

To 1200 g. of material containing 75.6 wt. % exo-2-hydroxy-1,4-cineole, 10.3 wt. % carvenone, 0.3 wt. % 4-hydroxycarvomenthone and 6.4 wt. % 3,7-dimethyl-2,6-octadiene, was added 277 g. of triethylenetetramine (TETA). The solution was fractionally distilled on a 4 ft.×2 in. glass column with Penn-state stainless steel protruded packing. The following table shows the results of the distillation.

| Fraction No. | Fraction Weight, g. | Kettle Temp. °C. | Head Temp. °C. | Reflux Ratio | Dist. Press. Head/Kettle | Analysis | | | |
|---|---|---|---|---|---|---|---|---|---|
| | | | | | | Light Ends | % Enone | % CNOH | % High Boilers |
| 1 | 46.4 | 125 | 98 | 20:1 | 5/20 | 71.3 | 4.4 | 22.1 | 2.2 |
| 2 | 43.9 | 123 | 95 | 20:1 | 5/16 | 13.2 | 11.6 | 73.9 | 1.2 |
| 3 | 50.2 | 125 | 100 | 20:1 | 5/16 | 0.7 | 4.5 | 94.2 | 0.6 |
| 4 | 53.4 | 125 | 99 | 20:1 | 4/18 | — | 1.0 | 98.5 | 0.4 |
| 5 | 20.0 | 124 | 92 | 2:1 | 5/17 | — | 0.5 | 99.2 | 0.3 |
| 6 | 676.9 | 175 | 96 | 2:1 | 4/15 | — | Tr | 99.7 | 0.3 |
| 7 | 60.0 | 190 | 114 | 2:1 | 1/11 | 0.2 | 6.1 | 80.8 | 13.0 |
| Column Hold Up | 90.0 | | | | | | | | |
| Bottoms | 379.7 | | | | | | | | |

Fractions 4 through 6 are blended to give 750.3 g. of 99+% 2-hydroxy-1,4-cineole, an 82.7 wt. % product yield based on 2-hydroxy-1,4-cineole contained in the above distillate. The overall accountability of the 2-hydroxy-1,4-cineole is 98.2%. Fractions 1 through 3 can be recycled to another distillation to recover more 2-hydroxy-1,4-cineole. The bottoms material can be further processed to recover the carvenone and the TETA.

EXAMPLE 7

To 2000 g. of material containing 67.7 weight % exo-2-hydroxy-1,4-cineole and 12.8 wt. % carvenone was added 461.7 g. of triethylenetetramine (TETA). The solution was fractionally distilled on a 4 ft×2 in. glass column with Penn-State stainless steel protruded packing. The following table shows the results of the distillation.

| Fraction No. | Fraction Weight, g. | Kettle Temp. °C. | Head Temp. °C. | Reflux Ratio | Overhead Press., mmHg | Analysis | | | |
|---|---|---|---|---|---|---|---|---|---|
| | | | | | | % Light Ends | % Enone | % CNOH | % High Boilers |
| 1 | 78.5 | 80 | 60 | Strip | 20 | (water) | | | |
| 2 | 49.5 | 130 | 97 | 20:1 | 5 | 4.7 | 3.7 | 89.9 | 1.7 |
| 3 | 42.2 | 130 | 96 | 20:1 | 5 | 7.3 | 6.9 | 83.6 | 2.6 |
| 4 | 52.3 | 132 | 102 | 20:1 | 4 | — | 2.3 | 95.3 | 2.4 |
| 5 | 52.2 | 132 | 104 | 20:1 | 6 | — | 2.2 | 97.3 | 0.5 |
| 6 | 52.7 | 132 | 104 | 20:1 | 5 | — | 0.4 | 98.7 | 0.9 |
| 7 | 69.3 | 134 | 102 | 20:1 | 5 | — | 0.3 | 99.0 | 0.7 |
| 8 | 55.2 | 134 | 102 | 20:1 | 5 | — | 0.1 | 99.3 | 0.7 |
| 9 | 839.4 | 171 | 104 | 2:1 | 5 | — | 0.1 | 99.4 | 0.5 |
| 10 | 136.0 | 190 | 110 | Strip | 5 | — | — | 95.3 | 4.7 |
| Hold Up | 71.1 | | | | | | | | |
| Bottoms | 729.0 | | | | | | | | |

Fractions 6 through 9 were blended to give 1017.6 g. of 99+% exo-2-hydroxy-1,4-cineole, a 75.5 weight % product yield based on exo-hydroxy-1,4-cineole contained in the above distillate. The overall accountability of the exo-2-hydroxy-1,4-cineole was 98.5%. Fractions 2 through 5 and fraction 10 can be combined and recycled to another distillation to recover additional exo-2-hydroxy-1,4-cineole. The bottoms material can be further processed to recover the carvenone and the TETA.

What is claimed is:

1. A method of purifying exo-2-hydroxy-1,4-cineole contaminated by admixture with a ketone, which comprises;

reacting the admixed ketone with an amine to obtain an enamine; and separating the exo-2-hydroxy-1,4-cineole from the enamine by distillation.

2. The method of claim 1 wherein said amine is triethylenetetramine.

3. The method of claim 1 wherein said amine is ethylenediamine.

4. The method of claim 1 wherein said amine is diethylenetriamine.

5. The method of claim 1 wherein said amine is polyaminopropylethylenediamine.

6. The method of claim 1 wherein said amine is monoethanolamine.

7. The method of claim 1 wherein water formed during the reaction is removed as it forms.

8. The method of claim 7 wherein said water removal is by azeotropic distillation.

9. A method of separating exo-2-hydroxy-1,4-cineole from a mixture with solvent hydrocarbons and ketone impurities, comprising;

reacting the ketone impurities in the mixture with an amine to obtain an enamine and water by-product;

distilling the reaction mixture to remove the water by-product and the solvent hydrocarbons; and further distilling the reaction mixture to obtain said exo-2-hydroxy-1,4-cineole free from said enamine.

10. The method of claim 9 wherein said amine is triethylenetetramine.

11. The method of claim 9 wherein said amine is ethylenediamine.

12. The method of claim 9 wherein said amine is diethylenetriamine.

13. The method of claim 9 wherein said amine is polyaminopropylethylenediamine.

14. The method of claim 9 wherein said amine is monoethanolamine.

15. A method of purifying exo-2-hydroxy-1,4-cineole contaminated by admixture with a ketone, which comprises;

reacting the admixture ketone with a reagent to form a water-soluble derivative of the ketone; and separating the derivative from the exo-2-hydroxy-1,4-cineole by water extraction.

16. The method of claim 15 wherein the reagent is a mixture of sodium bisulfite and sodium bicarbonate.

17. The method of claim 15 wherein the reagent is (carboxymethyl)trimethylammonium chloride hydrazide.

* * * * *